US008597187B2

(12) United States Patent
Nuccitelli et al.

(10) Patent No.: US 8,597,187 B2
(45) Date of Patent: *Dec. 3, 2013

(54) HAND-HELD ELECTRIC FIELD IMAGER FOR MEASURING THE SURFACE TOPOGRAPHY OF MAMMALIAN SKIN AND OTHER EPITHELIAL STRUCTURES

(75) Inventors: Richard Lee Nuccitelli, Millbrae, CA (US); Pamela Nuccitelli, Millbrae, CA (US); Suman Narsing, Herndon, VA (US); Brian Athos, Pleasanton, CA (US); Saleh Sheikh, Hampton, VA (US)

(73) Assignee: BioElectroMed Corp., Burlingame, CA (US)

( * ) Notice: Subject to any disclaimer, the term of this patent is extended or adjusted under 35 U.S.C. 154(b) by 412 days.

This patent is subject to a terminal disclaimer.

(21) Appl. No.: 12/484,971

(22) Filed: Jun. 15, 2009

(65) Prior Publication Data

US 2010/0016686 A1    Jan. 21, 2010

Related U.S. Application Data

(63) Continuation-in-part of application No. 11/031,188, filed on Jan. 7, 2005, now abandoned.

(60) Provisional application No. 61/082,173, filed on Jul. 18, 2008.

(51) Int. Cl.
*A61B 5/103* (2006.01)

(52) U.S. Cl.
USPC .......................................... 600/306; 600/300

(58) Field of Classification Search
USPC ................. 600/300, 306; 324/754.02, 754.05
See application file for complete search history.

(56) References Cited

U.S. PATENT DOCUMENTS 4,602,639 A * 7/1986 Hoogendoorn et al. ...... 600/372
4,805,600 A   2/1989 Wess et al.
(Continued)

FOREIGN PATENT DOCUMENTS

EP          714629 A1    6/1996
WO    WO 01/90730 A2 * 11/2001    .............. G01N 25/00
(Continued)

OTHER PUBLICATIONS

"Potential Control Under Thin Aqueous Layers Using a Kelvin Probe". Available online Dec. 18, 2006. Corrosion Science 49 (2007) 2021-2036.*

(Continued)

*Primary Examiner* — Navin Natnithithadha
*Assistant Examiner* — Meredith Weare
(74) *Attorney, Agent, or Firm* — Kilpatrick Townsend & Stockton LLP

(57) ABSTRACT

The present invention provides a hand-held, noninvasive diagnostic device for measuring the electric fields in mammalian skin and other epithelial structures. The device includes an outer housing that contacts the skin, providing stability and allowing the device to move along with minor movement of the skin. Recessed within the outer housing is a probe that acts as a sensor to measure the electric field in the skin through an aperture in the bottom surface of the outer housing. By applying a series of known voltages while the probe is vibrating, the skin's local surface potential can be measured and the lateral electric field can be calculated from the spatial distribution of surface potential measurements. Active feedback is used to maintain a constant distance between the probe and the skin surface.

20 Claims, 9 Drawing Sheets

(56) References Cited

U.S. PATENT DOCUMENTS

| | | | |
|---|---|---|---|
| 4,846,184 A * | 7/1989 | Comment et al. | 600/306 |
| 5,241,276 A * | 8/1993 | Tanaka et al. | 324/452 |
| 5,369,370 A * | 11/1994 | Stratmann et al. | 324/663 |
| 5,438,206 A * | 8/1995 | Yokoyama et al. | 250/442.11 |
| 5,640,240 A * | 6/1997 | Butler et al. | 356/624 |
| 5,830,177 A | 11/1998 | Li et al. | |
| 6,201,227 B1 * | 3/2001 | Tomita | 250/201.3 |
| 6,500,131 B2 * | 12/2002 | Leitner et al. | 600/594 |
| 6,807,438 B1 | 10/2004 | Brun Del Re et al. | |
| 7,126,343 B1 * | 10/2006 | Howes et al. | 324/446 |
| 2002/0133097 A1 * | 9/2002 | Leitner et al. | 600/594 |
| 2004/0034297 A1 | 2/2004 | Darrow et al. | |
| 2004/0092802 A1 * | 5/2004 | Cane et al. | 600/306 |
| 2005/0154270 A1 * | 7/2005 | Nuccitelli et al. | 600/345 |
| 2009/0281411 A1 * | 11/2009 | Nuccitelli et al. | 600/407 |

FOREIGN PATENT DOCUMENTS

| | | |
|---|---|---|
| WO | WO 02/13690 | 2/2002 |
| WO | WO 2005/070073 | 8/2005 |
| WO | WO 2010/008720 | 1/2010 |

OTHER PUBLICATIONS

PCT International Application No. PCT/US2009/047368 filed Jun. 15, 2009 in the name of Nuccitelli et al., International Search Report and Written Opinion mailed Jul. 29, 2009.

Baikie, I.D. and P. J. Estrup, "Low cost PC based scanning Kelvin probe," *Review of Scientific Instruments*, vol. 69, No. 11, pp. 3902-3907, 1998.

Baikie, I.D., P. J. S. Smith, D. M. Porterfield, and P. J. Estrup, "Multitiple scanning bio-Kelvin probe," *Review of Scientific Instruments*, vol. 70, No. 3, pp. 1842-1850, 1999.

Baikie, I.D., S. Mackenzie, P. J. Z. Estrup, and J. A. Meyer, "Noise and the Kelvin method," *Review of Scientific Instruments*, vol. 62, No. 5, pp. 1326-1332, 1991.

Blüh et al., "Vibrating Probe Electrometer for the Measurement of Bioelectric Potentials," *Review of Scientific Instruments*, Oct. 1950; 21(10):867-868.

Office Action issued for Australian Patent Application No. 2005206735 in the name of Nuccitelli et al., mailed Dec. 15, 2009.

Scheffrey, Local Transepithelial Current measurement by Vibrating Probe, 1987, IEEE, p. 403-406.

* cited by examiner

HAND-HELD ELECTRIC FIELD IMAGER FOR MEASURING THE SURFACE TOPOGRAPHY OF MAMMALIAN SKIN AND OTHER EPITHELIAL STRUCTURES

CROSS-REFERENCE TO RELATED APPLICATIONS

This application claims the benefit of U.S. Provisional Application No. 61/082,173, filed Jul. 18, 2008, which is incorporated herein by reference in its entirety; this application is also a continuation-in-part of U.S. application Ser. No. 11/031,188, filed Jan. 7, 2005 now abandoned.

FIELD OF THE INVENTION

This application is directed to a device for acquiring information from skin and other epithelia, and particularly to a hand-held device for measuring the surface topography of skin or other epithelial structures.

BACKGROUND OF THE INVENTION

There is a need for the accurate measurement of skin surface features such as the depth, height and width of wrinkles and skin lesions. This is important for measuring the effectiveness of medical treatments for skin diseases or in dermocosmetics to evaluate the effectiveness of anti-wrinkle treatments. Of particular difficulty is the accurate and rapid measurement of the depth of skin furrows. Most of the current methods for measuring depth are based on profilometric analyses requiring a polymer replica of the skin surface that is quite time consuming to carry out (Jacobi et al., 2004; Rosen et al., 2005). In recent years optical devices have been successfully employed to measure the skin surface directly but these are quite expensive and usually found in hospitals or research institutes. An inexpensive portable capacitative device has also been used to image the surface of skin (Bevilaequa et al., 2006). This approach provides good measurements of interwrinkle distance but does not provide accurate measurements of wrinkle depth.

SUMMARY OF THE INVENTION

A system that can be adapted to provide good wrinkle measurement depth at a reasonable cost is described in co-pending commonly owned patent application entitled "Application of the Kelvin Probe Technique to Mammalian Skin and Other Epithelial Structures," (U.S. patent application Ser. No. 11/031,188), filed on Jan. 7, 2005, incorporated herein by reference. That application describes a Bioelectric Field Imager (BFI) where a probe detects electric fields in the skin without contacting the region being studied by forming a parallel-plate capacitor between the skin and a sensor tip, then vibrating the sensor tip and taking measurements to determine the electric field. That method continuously tracks the distance between the sensor and the skin and adjusts that distance using a "z" motor to maintain the distance constant during electric field measurement. According to the present invention, by tracking the z motor steps required to maintain a constant distance between probe and skin, a surface topography of the skin is obtained over the scan region.

Although the BFI described in the '188 application is a very effective system, it is a bench-mounted device and is designed to perform scans in the x-y plane on horizontal, motionless surfaces, which generally requires that subjects be placed under anesthesia. Because of the risks associated with this requirement, the BFI is not optimum for general, routine use on human subjects. In addition, because of the physical constraints, the BFI is not ideal for use in medical offices or other outpatient settings.

Accordingly, we have filed a second copending patent application entitled, "Hand-held electric field imager for measuring the electric field in mammalian skin and other epithelial structures" (U.S. patent application Ser. No. 12/117,598, filed on May 8, 2008), incorporated herein by reference. That application describes a portable version of the BFI that overcomes the problems in the conventional techniques and provides additional features that make measuring the electric field in mammalian skin easier and more convenient. This new device can measure the electric field non-invasively and without the use of anesthesia to immobilize the subject. It is hand-held and can be easily manipulated to contact surfaces at a variety of orientations. It can adapt to the small continuous motions of mammals and be suitable for monitoring wound healing and for examining skin features such as wrinkles. The device of the '598 application also relies on a "z" motor to maintain a constant distance, and the z motor steps can be tracked to provide a skin topography in accordance with the present invention.

The present invention thus provides a hand-held, noninvasive diagnostic device for measuring the surface topography in mammalian skin and other epithelial structures. An embodiment of the invention provides a device that measures the surface topography in the skin of a subject at any angle while minimizing the risk and discomfort to the subject. In another embodiment of the invention, the device evaluates the surface topography surrounding a wound or skin lesion. In further embodiments, the device monitors healing of a wound in the skin or examines features of the skin, such as wrinkles.

The device includes a probe that acts as a sensor to measure the electric field in the skin and distance from the surface of the skin. The probe is positioned inside an outer housing, with the housing placed in contact with the surface of the skin to be examined and the probe recessed within the housing such that the probe does not contact the skin. A vibration unit is coupled to the probe and causes the probe to vibrate in the direction roughly perpendicular to the surface being examined. Vibration units that can produce high speed vibration, such as piezoelectric disks or electromagnetic speakers that produce frequencies of 800 to 1200 Hz, are preferred because the higher vibration frequencies produce stronger signals. The amplitude of the vibration (defined as half of the total vertical displacement of the probe) is preferably 90 µm or less, and more preferably in the range of 20-90 µm.

The probe comprises a conductive metallic tip that forms a parallel-plate capacitor with the skin surface. If the surface potential of the metal piece is different from the surface potential of the skin near it, there will be a build-up of charge on the "plates" of the capacitor. A microcontroller applies a series of known reference voltages ($V_b$), preferably ±5-10 V, to the metal probe or to the skin. The applied voltages induce a flow of charge between the two surfaces when they arc connected. Because the probe is vibrating, which varies the capacitance, the flow of charge, or current oscillates. The oscillating current is measured by a meter in the probe tip and then immediately converted to an oscillating voltage, which is transmitted to the microcontroller. From the oscillating voltage signal, the peak-to-peak voltage values are used to determine the voltage value at which there is no current flow between the two surfaces, which will be equal to the surface potential of the skin at that point. The microcontroller determines the peak-to-peak voltage values in hardware using either analog integration or a peak detector, rather than in software as in the BFI device, which reduces noise spikes and allows faster data acquisition.

These voltage measurements must all be made at the same distance from the skin. Therefore, a z-axis stepper motor is used to maintain this distance constant using feedback from the computer. By plotting the probe signal at two different bias voltages, we can obtain a direct measure of this distance between the probe and the skin and this is used to control the position of the probe as explained in detail below. By monitoring the z steps needed to maintain this constant distance we can obtain the surface topography of the skin being scanned.

The outer housing in which the probe is positioned is held in contact with the skin surface being examined to provide stable positioning for the probe, keeping the probe in the same frame of reference as that skin surface such that the probe stays in approximately the same position and orientation with respect to the skin. Because the outer housing rests on the skin surface, it moves with the skin, allowing the entire device to move with the skin as well. The outer housing includes an optically transparent lens as its bottom surface, which is the surface in contact with the skin. The lens has an aperture, or opening, over which the probe is positioned and through which the measurements are taken.

The aperture is preferably a narrow slit, most preferably about 1 mm wide, because this size and shape causes a minimal amount of protrusion of the skin into the aperture. It is important to minimize protrusion of the skin into the aperture to provide a substantially flat skin surface for accurate measurements, as further discussed below. Other shapes may be used for the aperture, particularly when examining skin that is relatively taut and not inclined to protrude up into the aperture. The aperture may also be covered with an electrically transparent material, which is a material that is non-conductive and does not interfere with the electric field, such as polyethylene or other polyvinyls. Covering the aperture is helpful when measuring the field at a wound site where any kind of fluid is present, such as blood or interstitial fluid, to avoid artifacts that interfere with accurate electric field measurements.

Two stepper motors control the positioning of the probe in relation to the skin being examined. The probe is moved parallel to the skin by means of a first miniature stepper motor that moves tile probe in increments of 10 μm within the housing from one end of the aperture to the other. The movement allows the probe to scan the region of skin exposed by the aperture to obtain the measurements necessary to determine the electric field for that region.

At the same time, a second miniature stepper motor controls the distance between the probe and the skin in the direction perpendicular to the skin surface (generally referred to as the "z" direction in this context). While the outer housing of the device provides stable positioning for the probe, as discussed above, the sensitivity of the capacitor requires substantial precision because the capacitance of the parallel-plate capacitor formed by the two surfaces is highly dependent on the amount of separation. Thus, the second stepper motor is required to provide this fine-tuned control mechanism. The second stepper motor continually adjusts the probe to maintain a constant distance between the probe and the skin in response to minor motions of the skin and to variations in the topography of the skin over the region scanned. By tracking the stepper motor movements required to maintain a constant distance between the probe and the skin, the surface topography of the skin can be determined and plotted for each "x" position.

Because of the importance of taking each measurement at the same distance from the epithelium being investigated, it is necessary to maintain a constant separation distance between the probe and the skin. Although it might appear contradictory to attempt to maintain this constant distance when the probe's position in the z direction is continually changing due to its vibration, it is possible to control the separation such that any given point in the path of the oscillation remains at the same distance from the epithelium. Thus, a constant distance is maintained by selecting a point in the oscillation path of the probe and maintaining that point at the same distance from the epithelium for all measurements. Here, the second stepper motor maintains the separation distance at which the probe tip is closest to the skin (the "distance of closest approach") at a constant value. The distance of closest approach is determined from the slope of a line drawn between two points: 1) −10 volts abscissa, the peak-to-peak sensor signal detected when −10 volts is applied to either the skin or the probe on the ordinate; 2) +10 volts on abscissa and that ptp signal detected when 10 volts is applied to either the skin or the probe on the ordinate. Specifically the distance between the sensor and the skin is inversely proportional to the slope of that line. This distance information is used to provide feedback to the second stepper motor to maintain a constant distance between the sensor and the skin. The second stepper motor establishes the probe's position in the z direction prior to taking measurements with the probe. The distance of closest approach is preferably 500 μm or less, more preferably in the range of 20-500 μm, and is preferably maintained to within a tolerance of approximately 6 μm.

DETAILED DESCRIPTION OF THE INVENTION

Figure 1:
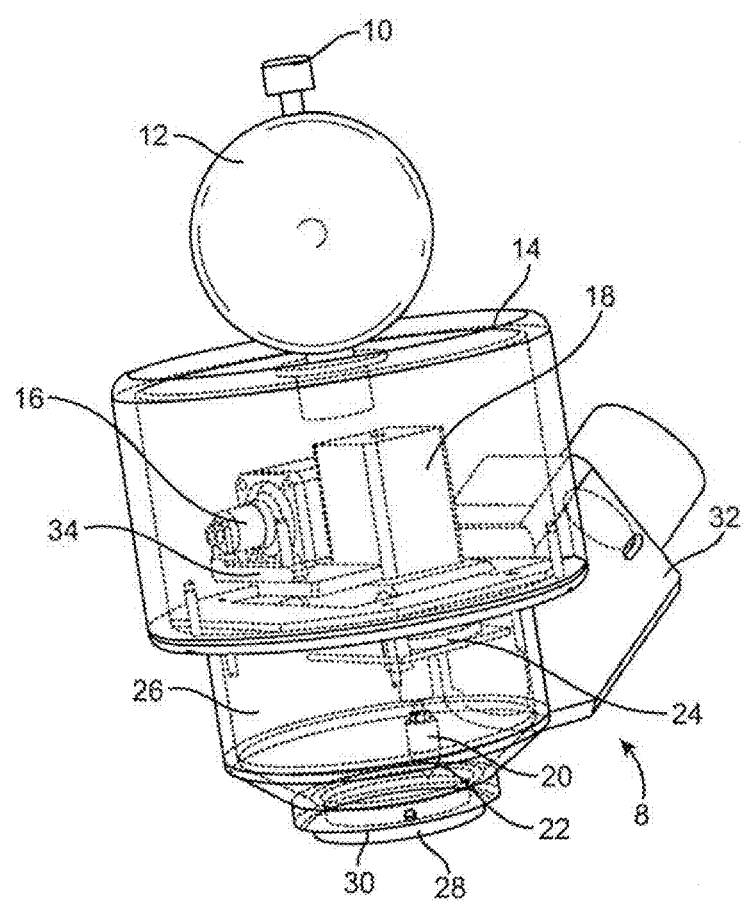
FIG. 1 depicts a partially transparent perspective view of the vibration unit assembly and sensor head of the device.

The present invention provides a device for measuring the surface topographies in epithelial tissue that is hand-held, noninvasive and suitable for use on human subjects, particularly for use in outpatient or other clinical settings. FIG. 1 shows a partially transparent perspective view of the hand-held device 8 according to an embodiment of the invention. As can be seen in the figure, there is a push-button actuator 10 at the top of the device attached to, and extending through, positioning handle 12. Positioning handle 12 is designed to be gripped by one hand of an operator in order to position and orient the device, thus it is preferably a spherical shape, but may be any other suitable shape for gripping. The arrangement of the positioning handle 12 with push-button actuator 10 allows an operator to activate and position the device with a single hand by wrapping a finger or fingers around the positioning handle 12 and engaging the push-button actuator 10 with a single finger. At the base of positioning handle 12 is cap 14 that covers and protects the motors 16 and 18, further discussed below.

Figure 5A:
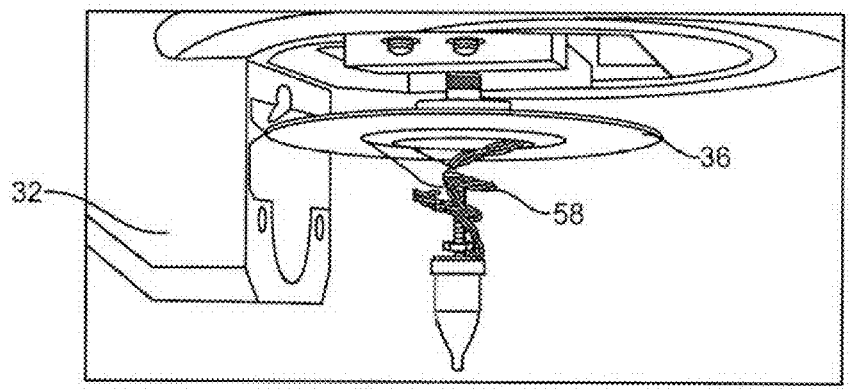
FIGS. 5A and 5B are photographs of the sensor tip mounted to two different vibration units.
Figure 5B:
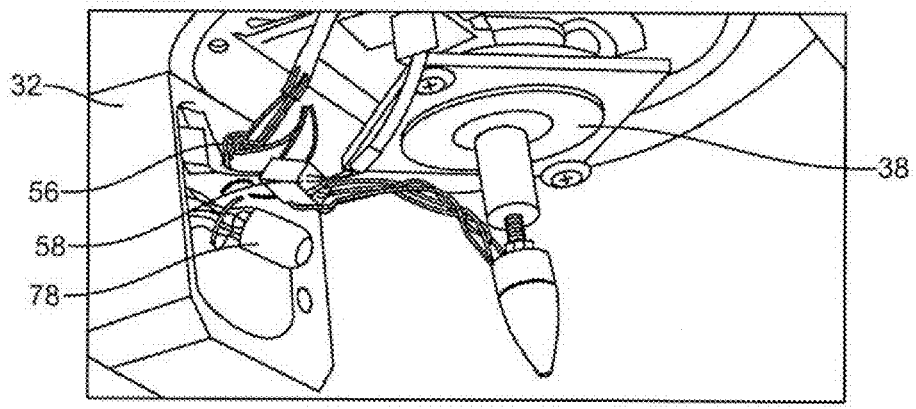
Figure 6A:
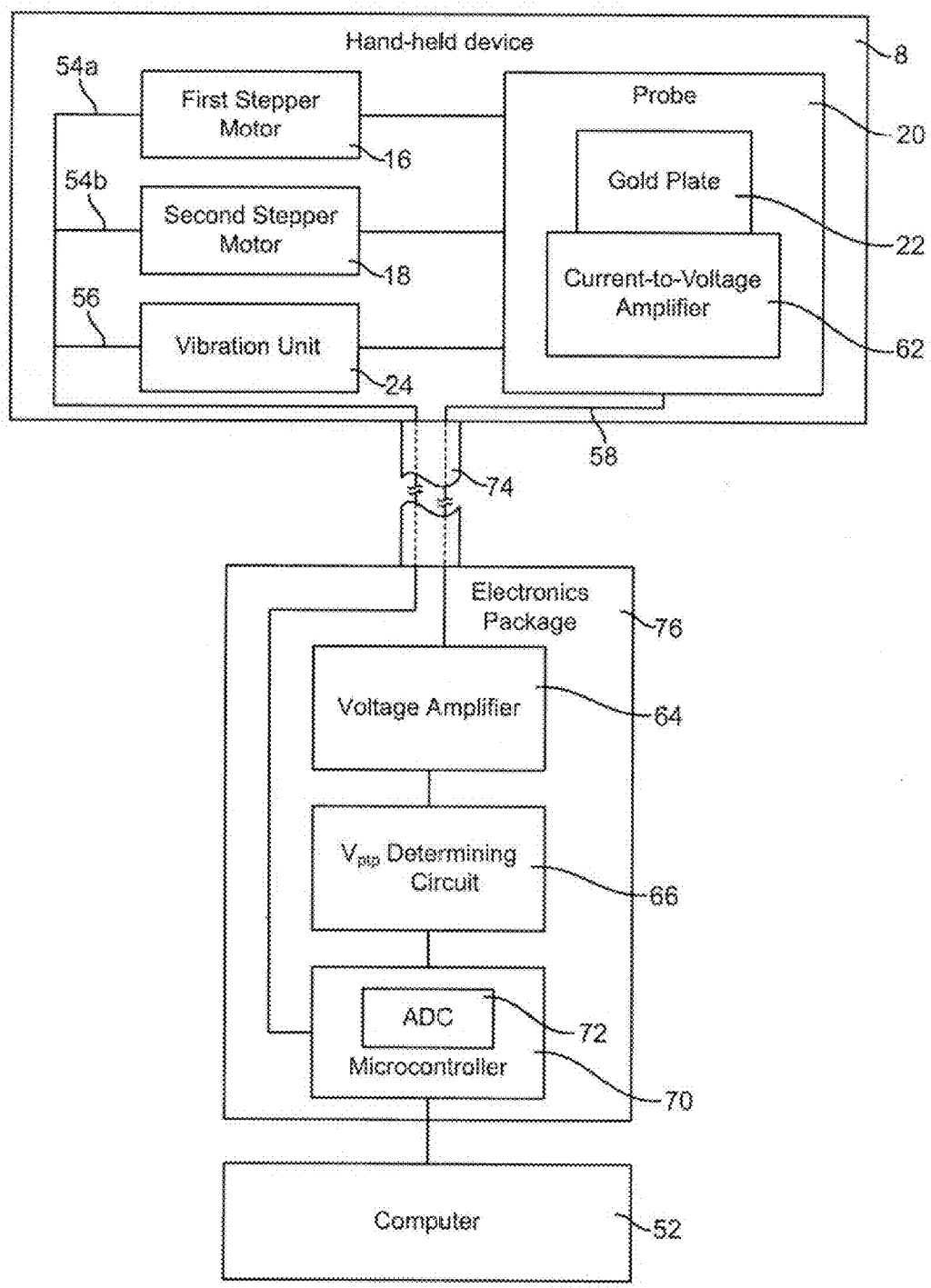
FIG. 6A shows a schematic diagram of the electronic elements and connections of the device.

Connected to the motors is probe 20, which contains sensing and processing electronics for the device, including a current-to-voltage amplifier circuit 62 (see FIG. 6A). Probe 20 is vibrated by a vibration unit 24 that may be either a piezoelectric disk or an electromagnetic speaker, shown in more detail in FIGS. 5A and 5B, respectively. As shown in FIG. 6A, the signal from the probe 20 is sent through a cable 74 to an electronics package 76, which is connected to a computer 52, where a microcontroller 70 and a $V_{ptp}$ determining circuit 66 analyze the capacitance formed between the gold plate 22 at the bottom tip of probe 20 and the epidermis of the subject (not shown in FIG. 1). The length of the connecting cable, which is usually several feet (e.g. a 6-ft. cable), allows the device to be easily positioned on any part of the subject being examined.

Figure 2:
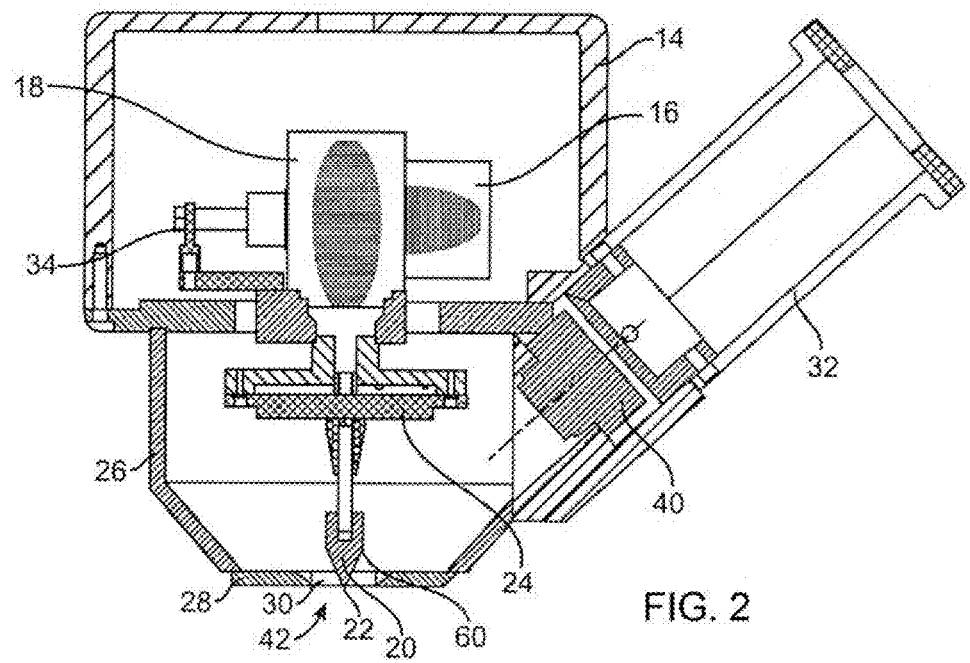
FIG. 2 shows a cross-sectional view of the body and connection handle of the device.

The lower portion of the device, including probe 20 and vibration unit 24, is enclosed in an outer housing 26 (FIGS. 1 and 2). Outer housing 26 is joined to cap 14, forming a covering for the body of the device, and is preferably formed from a plastic material. The bottom of outer housing 26 rests on the skin of the subject and this contact provides stable positioning of the device with respect to the skin surface being examined. Using positioning handle 12, the device may be positioned such that outer housing 26 is placed against a body surface having any orientation. In addition, having outer housing 26 in contact with the skin allows the device to move with the skin as the skin moves due to breathing, circulation, movement of the underlying muscles, or other movement. This matched movement permits the outer housing to hold the skin in a relatively stationary position with respect to the probe 20 and maintains the separation between the skin and sensor tip at a roughly constant distance, which allows the probe 20 to be positioned independently of minor involuntary movement by the subject. Of course, the subject should avoid large movements during scanning to allow the outer housing 26 to be held against the skin.

Figure 3:
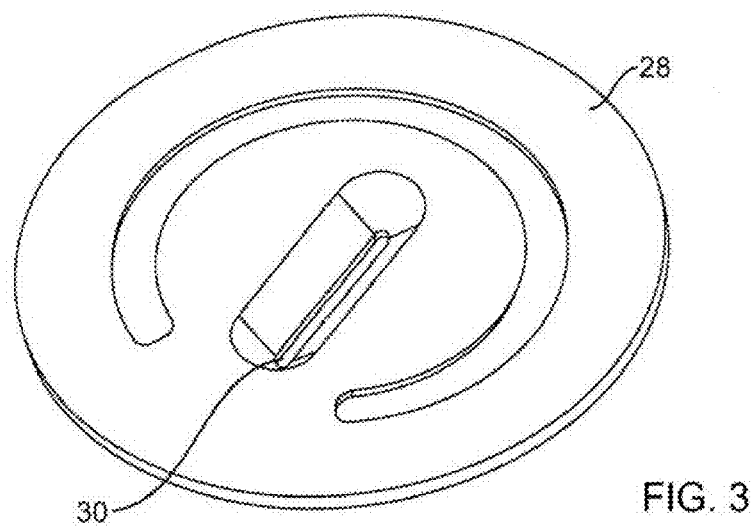
FIG. 3 depicts a perspective view of the lens and aperture in accordance with one embodiment of the present invention.

The bottom surface of outer housing 26 comprises a lens 28 that is formed from a transparent material and has an aperture 30 (shown in more detail in FIGS. 2 and 3). Aperture 30 provides access to the skin for the probe 20 to scan and is preferably a slit about 1 mm wide. The preferred narrow width of the aperture 30 optimizes the surface topology for scanning because it minimizes the amount of skin that protrudes up into the aperture. When skin protrudes up into the aperture, it has a convex shape, thus the separation distance between the skin and the probe 20 is not the same for the entire region of skin exposed by the aperture. Variations in the separation distance makes positioning of probe 20 in the z direction difficult, and has an adverse affect on the quality of the measurements taken, as further discussed with respect to the positioning mechanism. Accordingly, the shape and dimensions of the aperture should be selected to minimize protrusion of the skin into the aperture. Thus, when measuring skin that is particularly loose and flexible, a narrow aperture will be preferred. In contrast, when examining a region of skin that is substantially taut, a larger aperture or an aperture of another shape may be acceptable.

When measuring the surface topography at a wound site that has any kind of fluid present, such as blood or interstitial fluid, the fluid can interfere with the accurate measurement of the epidermal surface potential by the device due to the differences in the work function characteristics of the fluid in comparison with those of the surrounding tissues. The work function, which is the minimum energy needed to remove an electron from the surface of a material, is very different for dry skin than for fluids. Thus, when moved from a position over dry skin to one over fluid, the probe will detect a large voltage difference that is due to work function differences alone, rather than from the electric field of interest that is generated by the current flow beneath the epidermis. The effect of these differences in work function can be minimized by placing a thin covering 42 (FIG. 2) over the aperture that is an electrically transparent material, such as polyethylene or other polyvinyls. With the covering 42 in place, the surface work function is the same for all positions scanned by the probe, while the underlying electric field is easily detected through the electrically transparent material.

The probe 20 examines the skin exposed by the aperture 30 as its position is controlled by the first stepper motor 16 in the x direction, which follows the length of aperture 30. In a preferred embodiment, adjustments in the y direction are not necessary because of the narrow width of aperture 30 (see FIG. 3). In addition, if measurements of regions to either side of the aperture 30 are required, the device may easily be repositioned such that the aperture 30 exposes those regions for subsequent scans. As shown in FIG. 2, first stepper motor 16 includes a positioning arm 34 that moves probe 20, along with vibration unit 24, incrementally in the x direction. The first stepper motor 16 is electrically connected to and controlled by the computer 52 (FIG. 6A) via signal wires 54a extending through connection handle 32 (FIG. 2). The first stepper motor 16 is capable of moving with a 40 μm step size and allows the collection of surface potential data over a linear region of the skin.

The second stepper motor 18 is responsible for maintaining the position of probe 20 in the z direction (FIG. 3), which is roughly perpendicular to the skin surface. The outer housing 26 and lens 28 keep the device steady with respect to movements of the skin; however, the device requires that the distance between the closest approach of probe 20 and the skin be precisely maintained in order to accurately determine the surface topography of the skin, thus the second stepper motor 18 provides the necessary fine adjustments. The feedback control mechanism employed by the second stepper motor 18 is discussed in further detail below. Vibration of the probe 20, caused by vibration unit 24, also occurs in the z direction, thus second stepper motor 18 controls the distance of closest approach, as defined above.

The vibration units used in the device are preferably either a piezoelectric disk 36 (FIG. 5A) or an electromagnetic speaker 38 (FIG. 5B). The piezoelectric disk is composed of two piezoelectric ceramics, each bonded to a brass disk, that are in turn attached together. The electromagnetic speaker is composed of a speaker element that vibrates on an axis normal to the skin or other epithelium. The vibration unit 24 vibrates probe 20 at 800 Hz or greater. Currently, frequencies in the range of 800 to 1200 Hz are used, but higher frequencies may be used as faster, quieter vibration techniques and devices are developed. In general, the highest frequency available is preferred as higher frequencies generate a stronger signal. The high frequency vibration used here represents an almost twenty-fold increase over the vibration frequency used in the bench-mounted BFI, allowing for faster data acquisition and overall shorter scanning times. This is advantageous for the subjects because it minimizes the time that they need to remain relatively still.

Figure 4:
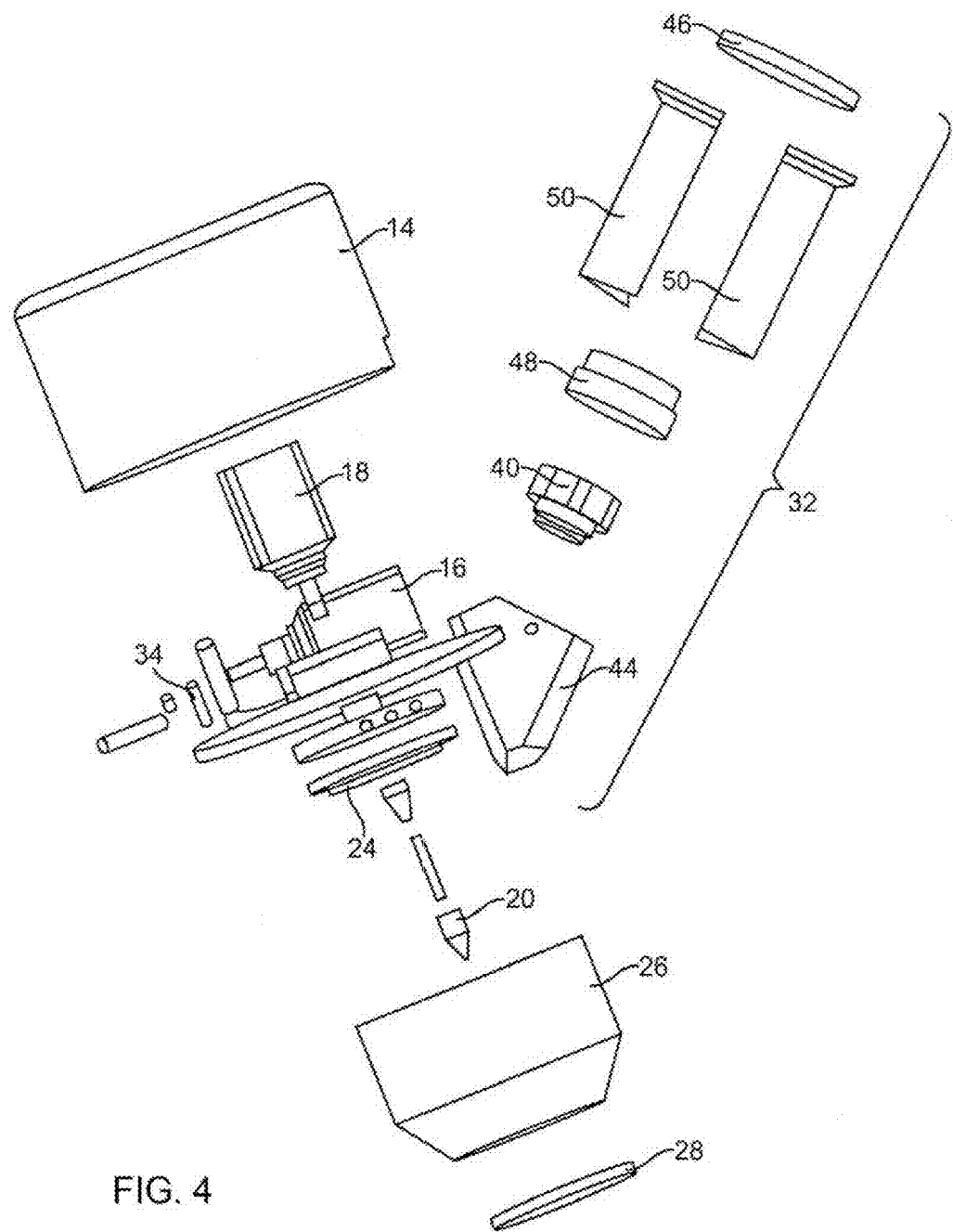
FIG. 4 shows an exploded view of the body and connection handle of the device.

FIGS. 2 and 4 show a color video camera 40 located inside connection handle 32 that allows the operator performing the scan to see the area over which the device is positioned. Connection handle 32 is comprised of a camera housing 44, right-hand and left-hand adapter rings 46 and 48, and a two part cylinder portion 50 (FIG. 4). The camera 40 images a view through lens 28, as shown in the upper right portion of the graphical interface depicted in FIG. 8. An LED (78 in FIG. 5B) provides illumination to the area. The camera display allows the device to be precisely positioned over a wound or a skin lesion, which reduces the number of scans that do not cover the intended region. In addition to housing camera 40, connection handle 32 provides a conduit for connection of the device to a computer 52 via cable 74 and the electronics package 76 (FIG. 6A). Signal wires extend into connection handle 32 (FIG. 2) from the motors 16 and 18 (54a and 54b in FIG. 6A), the vibration unit 24 (56 in FIG. 6A) and the probe 20 (58 in FIG. 6A).

Returning to FIG. 2, probe 20 has an outer portion 60 that forms a conductive metal layer that electrically shields the electronics inside and the gold plate 22 at the bottom. The gold plate 22 and the subject's epidermis (not shown in FIG. 2) form plates of a parallel-plate capacitor. Because the surface potential of each plate is different, charges will build up on the plates and a voltage will develop across the capacitor (the contact potential). A series of reference (biasing) voltages of ±5-10 V, preferably ±10 V, are applied to either the skin or to the gold plate 22, which causes the charges on the plates to change, meaning that a current flows from one plate to the other via the connection formed across the applied voltage. In a preferred embodiment, the reference voltages are applied to the skin via a conventional skin surface electrode (such as those used in electrocardiography). Application of the reference voltage to the skin results in fewer switching artifacts compared with application to the probe, which allows data acquisition to begin more quickly.

The reference voltages are applied in pairs (e.g. +10 V and −10 V) in an alternating sequence during the measurement period. At the same time, the probe 20 is vibrated in the z direction by vibration unit 24, changing the distance separating the plates of the capacitor. The capacitance of a parallel-plate capacitor depends on the distance between the plates, thus the capacitance is very sensitive to changes in that distance. As the capacitance changes, the charge on the plates is also changed in accordance with the equation Q=CV (here, voltage can be assumed to be relatively constant). The current corresponds with the change in charge over time, given by i=dQ/dt, thus the combination of the applied voltage and vibration of the probe induce an oscillating current.

In one embodiment of the present invention, the oscillating current is measured by the probe 20 and immediately converted to a voltage via a current-to-voltage or transimpedance amplifier 62 (FIG. 6A). To reduce the input capacitance of the current-to-voltage amplifier 62, the gold plate 22 is mounted directly on the amplifier chip and the chip is embedded in plastic and shielded. The output voltage of the amplifier varies periodically as the probe vibrates (an oscillating voltage), and the peak-to-peak voltage ($V_{ptp}$) depends on the difference between the contact potential and the reference voltage. The signal from the probe 20 is sent via cable 74 to an electronics package 76, where the signal is further amplified through a voltage amplifier 64 to generate an amplitude of approximately 2 V peak-to-peak. The amplified signal is then sent to a circuit 66, where one of two methods may be used to determine the $V_{ptp}$.

Figure 6D:
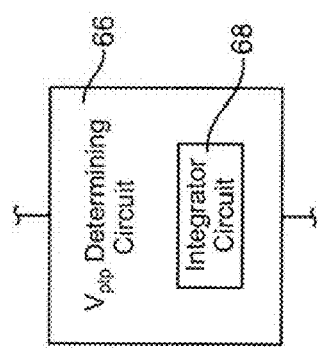
FIG. 6B-6D show three variations on the circuit used to determine the $V_{ptp}$.
Figure 6C:
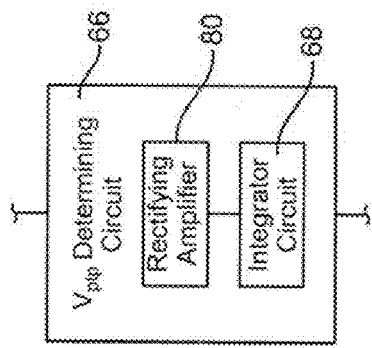
Figure 6B:
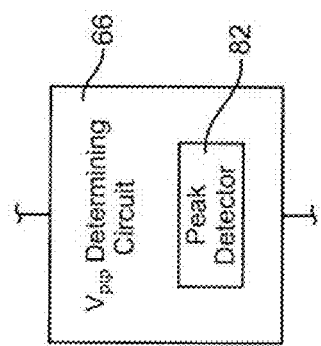

In the first method, the oscillating voltage is accumulated over a fixed sample time by an integrator circuit 68 (FIG. 6B). Because the voltage signal is oscillating about 0 volts, it is necessary to invert the signal from negative to positive when the signal is in the negative range in order to integrate. The microcontroller 70 instructs the integrator circuit 68 to invert the signal at the appropriate times in this phase-dependent inversion method. The then-positive signal allows the integrator circuit 68 to sum the total area between the voltage wave and the time axis. Integrator circuit 68 integrates the signal for a fixed number of periods, beginning from the minimum signal level, which is zero in this ease, further reducing noise. The integrated signal is proportional to the peak-to-peak value of the vibrating capacitor-induced signal. In an alternative embodiment, the signal may be rectified by an amplifier 80 (e.g. an AD8037, a wide bandwidth, low distortion clamping amplifier) before integration, such that the negative portions of the signal are reflected about the time axis (x-axis) and made positive (FIG. 6C). However, the rectified signal tends to have a lower signal-to-noise ratio compared to the signal produced using phase-dependent inversion.

In the second method, a peak detector circuit 82 averages the positive peak signals and the negative peak signals (FIG. 6D). This method is less sensitive to slight changes in frequency than the integration method, while providing a high signal-to-noise ratio.

The output of the integrator circuit 68 or peak detector 82 is sensed by the microcontroller 70 via an analog-to-digital converter (ADC) 72 (FIG. 6A). Datasets are measured and transmitted from the microcontroller 70 to the computer 52 at a rate of approximately 21 Hz. Each dataset consists of a data value and integration time versus each applied reference voltage (e.g. a data value and integration time for the +10 V reference and a data value and integration time for the −10 V reference). From the datasets, the average $V_{ptp}$ for each reference voltage is calculated and plotted against the reference voltage values. The resulting line will intercept the reference voltage axis at a point that corresponds to the voltage at which there would be no current flow between the two surfaces, which also provides the voltage created by the electric field of the subject's skin at the location measured. As described above, after determining the surface potential at several points in a given region, the electric field between any two points is given by the difference in surface potential at these points divided by the distance between them.

In addition, the line of $V_{ptp}$ plotted against the reference voltages is used in the control of the positioning of the probe 20 in the z direction by second stepping motor 18. The slope of the line is inversely proportional to the distance between the closest approach of the probe and the skin surface, thus by maintaining the slope, the distance is also maintained. The computer 52 uses the slope data to send feedback signals to the second stepper motor 18 via the microcontroller 70. When the slope varies from a target slope value, the computer 52 provides the slope information to microcontroller 70, which generates a control signal for the second stepper motor 18 to adjust the z position of probe 20 before each measurement. The data sampling rate of 21 Hz allows the microcontroller 70 to provide the control signal to the second stepper motor 18 at a rate of 1-5 Hz, as a proportional controller. The amount of adjustment of the probe's position is based on the slope value at that time compared to the target slope value. The stepper the slope of the line, the more change will result from a given adjustment of the probe. Accordingly, the computer 52 continually monitors the separation distance as it evaluates new datasets and produces the line of $V_{ptp}$ plotted against the reference voltages. The surface topography is then displayed by plotting the z motor step adjustments required to maintain the constant distance between the probe and the skin.

Figure 7:
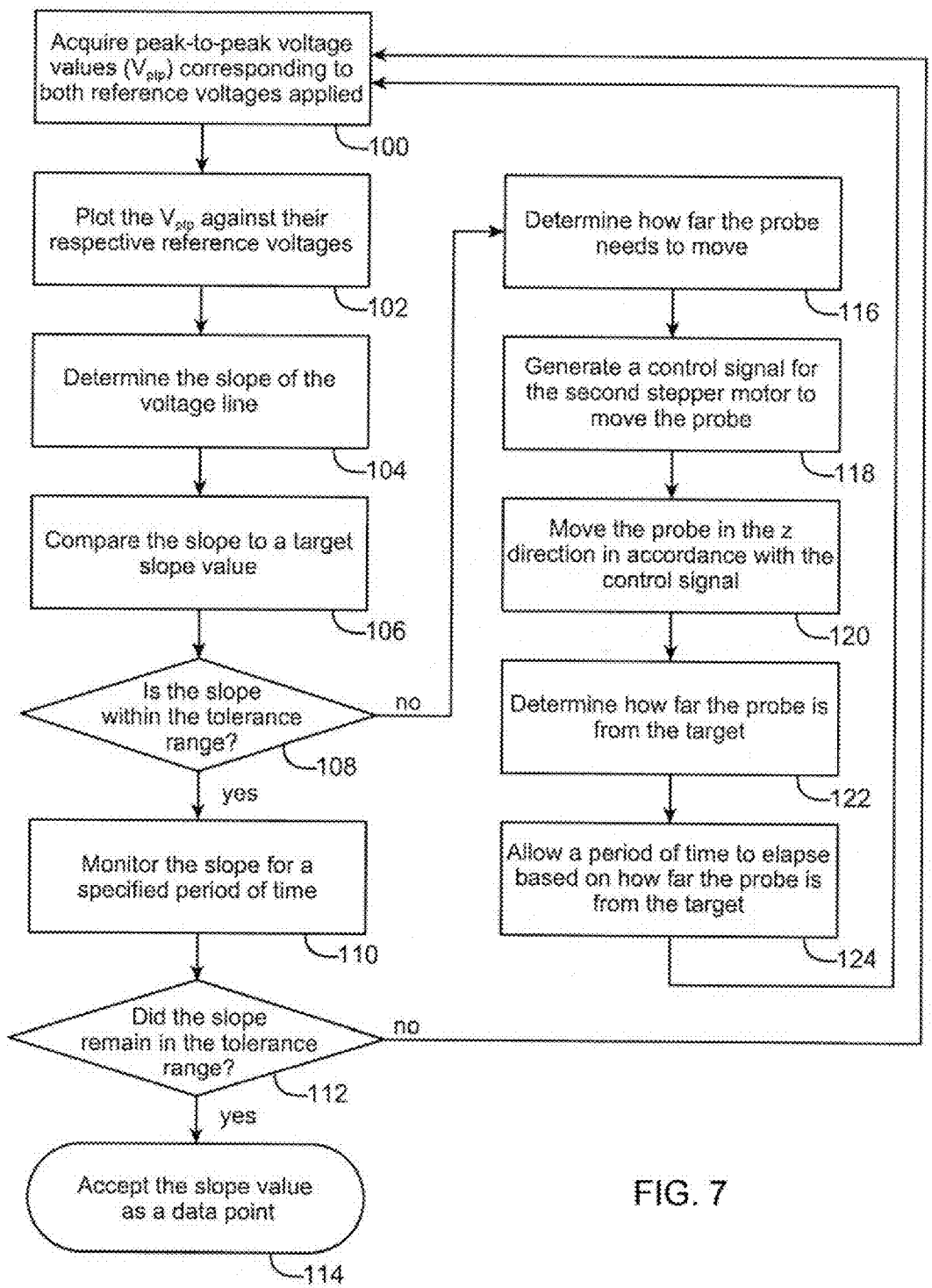
FIG. 7 is a flow chart illustrating the feedback control mechanism for the second stepper motor.

As shown in more detail in the flowchart of FIG. 7, the feedback control mechanism begins with the acquisition of the calculated average $V_{ptp}$ values 100. As described above, these values are then plotted against their corresponding reference voltages 102. The slope of the voltage line is determined 104 and compared with a target slope value 106. The feedback control mechanism next determines if the slope is within the tolerance range 108. If it is in the tolerance range, the slope is monitored for a predetermined amount of time 110 to ensure that it remains in the range. If it remains in the range as evaluated at step 112, then the slope can be accepted as a data point 114 and measurements may be taken in order to determine the electric field of the epithelium. As stated above, the position of the probe in the z direction must be established prior to taking any measurements. If the slope does not remain within the tolerance range for the specified period, then the process begins again at step 100 as new $V_{ptp}$ values are acquired.

If the slope was determined not to be in the tolerance range at step 108, then the microcontroller 70 determines how far the probe needs to be moved 116 and generates the appropriate control signal 118 for the second stepper motor 18. The second stepper motor 18 then moves the probe in accordance with the control signal 120. Next, the microcontroller 70 determines how far the probe is from the target 122 and allows a period of time to elapse based on that determination 124. If the probe is far from the target, a short amount of time is required, but if the probe is close to the target, then the amount of time is longer. This variable waiting time allows the slope to stabilize when it is near the target (where it is most important), but also allows the probe to be moved quickly when it is farther away. After the time period has elapsed, the control mechanism returns to step 100 to acquire new $V_{ptp}$ values to continue to evaluate the slope until the positioning of the probe in the z direction is acceptable.

Because the microprocessor 70 generates the control signals for the second stepper motor 18 based on feedback from the probe itself, it is important that the probe's signal contains accurate information about the distance between the probe and the skin surface. The surface topology of the skin can be rather complex near wounds, lesions, and wrinkles thus the distance between the skin and the probe must be adjusted before every measurement to ensure that the distance of closest approach is maintained.

Figure 8:
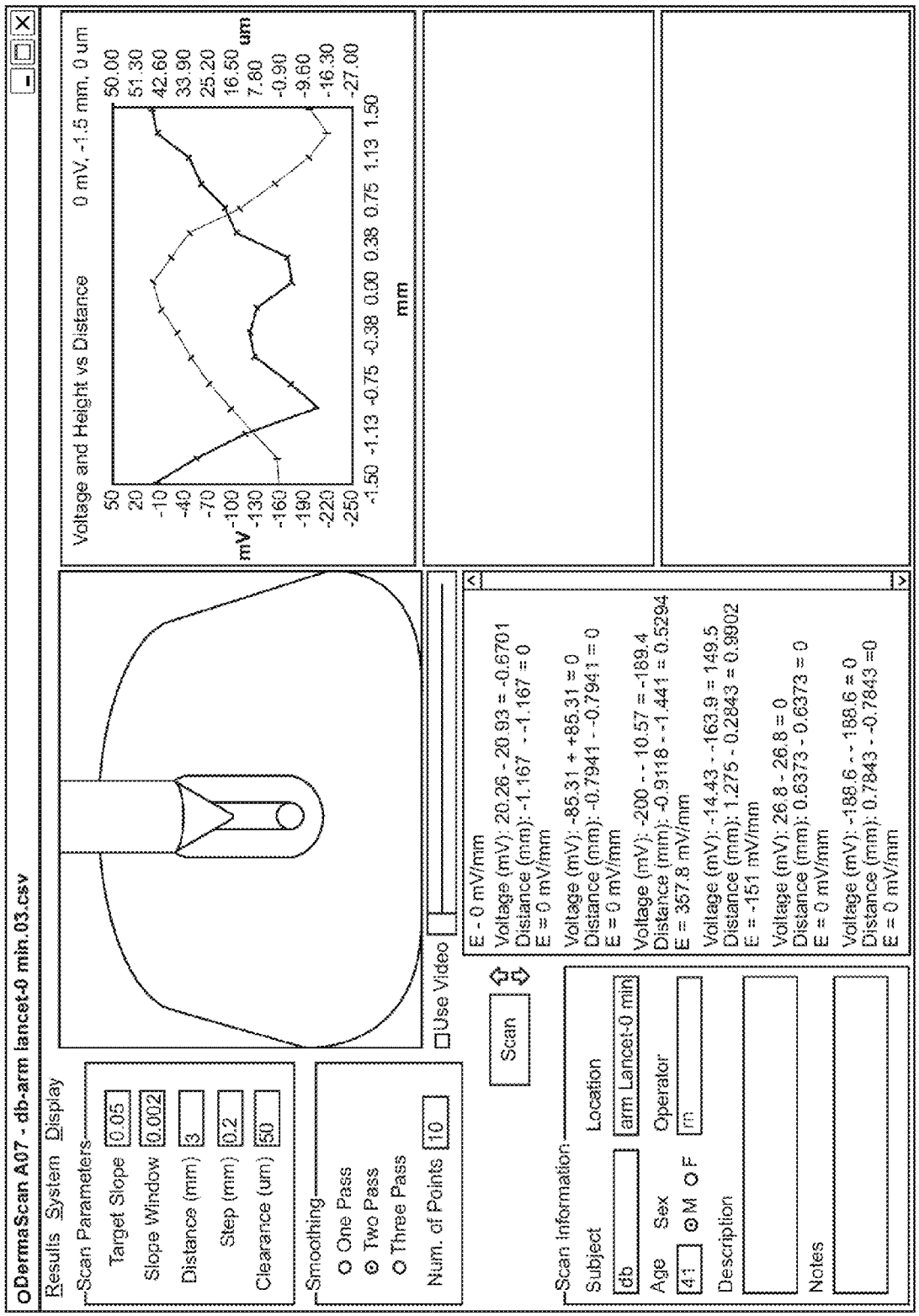
FIG. 8 depicts one embodiment of a graphical interface for the present invention used on a computer.

FIG. 8 depicts one embodiment of a graphical interface used on the computer. In the top center panel a real-time video image from camera 40 of the probe 20 and the epithelium being scanned is displayed. To the right of the video image, the probe's real-time output is displayed as it scans across a lancet wound. The average surface potential is displayed in blue (peaking downwardly) and the topographical information is displayed in red (peaking upwardly). The increase in potential present as the device scans-over the wound indicates a lateral electric field on either side of the wound region and the red plot indicates that the wound region is higher that the surrounding surface probably due to swelling of the wounded dermis.

Figure 9A:
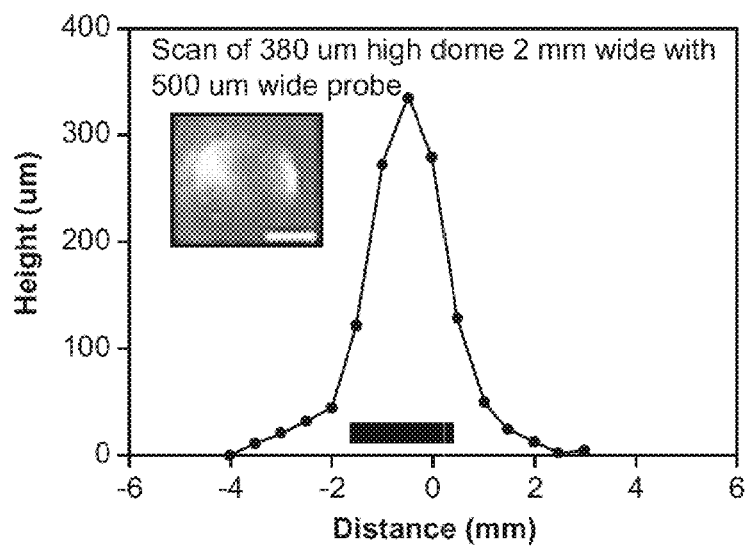
FIG. 9A depicts a Dermacorder scan of a dome feature that is 380 um high at the center and 2 mm wide at the base. The probe tip size used for this scan was a disk 500 um in diameter.
Figure 9B:
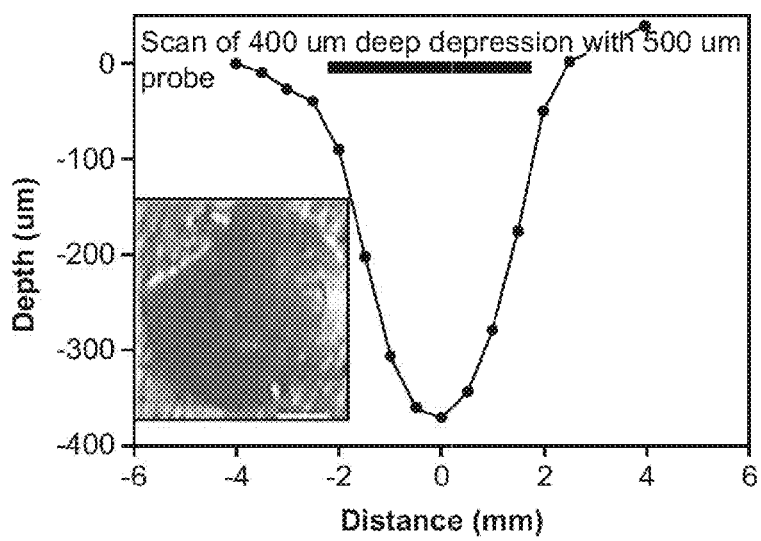
FIG. 9B depicts a Dermacorder scan of a 400 um deep depression that is 4 mm wide. The probe tip size was a disk 500 um in diameter.
Figure 9C:
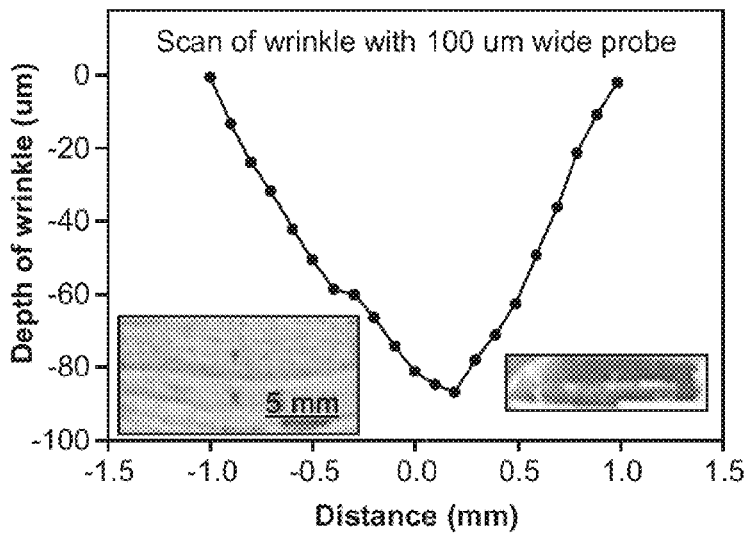
FIG. 9C depicts a Dermacorder scan of a human skin wrinkle using a probe that was 100 um wide by 2 mm long.

FIGS. 9A-9C show scans of different surface profiles. FIG. 9A shows the Dermacorder scan of a 2 mm wide dome shape that is 380 um high in the center. It was scanned using a probe tip that was a disk 500 um in diameter. The red bar indicates the position of the dome on this plot and the inset shows a photograph of the dome with a scale bar indicating 1 mm. FIG. 9B shows the Dermacorder scan of a 4 mm wide depression that is 400 um deep in the center scanned with the same probe described in 9A. The red bar indicates the position of the depression. FIG. 9C shows the Dermacorder scan of a forehead wrinkle shown in the left inset. The probe used here was 100 um by 2 mm long as shown in the right inset. The scale bar in the right inset is 1 mm long. A polymer replica of this wrinkle indicated a depth of 160 um. That the Dermacorder measured only 90 um is due to the fact that resting the Dermacorder on the skin tends to flatten the wrinkle profile somewhat.

In additional embodiments of the invention, a series of measurements are taken in the x direction in order to obtain data in two dimensions, rather than the linear measurements described above. In one embodiment, the probe 20 is replaced by multiple probes in order to provide simultaneous measurements at multiple locations. In another embodiment, the probe 20 is provided with multiple sensors to achieve similar measurements.

The invention claimed is:

1. A noninvasive diagnostic device for measuring a surface topography associated with an epithelium of a mammal comprising:
    a hand-held outer housing having a bottom surface that includes an aperture, wherein the bottom surface is adapted to contact an epithelium of a mammal such that the outer housing moves with a movement of the epithelium;
    a probe recessed within the outer housing and positioned above said aperture, the probe comprising a conducting plate;
    a vibration unit attached to said probe configured to vibrate said probe over the epithelium of the mammal, wherein the vibration of the probe defines an oscillation path of the probe;
    a voltage supply configured to create a voltage bias between the probe and the epithelium;
    a positioning device having a first motor attached to the hand-held outer housing configured to move the probe in an x direction with respect to the outer housing aperture, and a second motor attached to the probe configured to maintain a substantially constant distance in a z direction between the epithelium and a point on the oscillation path of the probe; and
    a system for recording or displaying travel of the positioning device second motor in the z direction, wherein said travel represents a surface topography of the epithelium.

2. The device as recited in claim 1, wherein the aperture is a slit.

3. The device as recited in claim 2, wherein said slit is about 1 mm wide.

4. The device as recited in claim 1, further comprising:
    an electrically transparent material covering the aperture.

5. The device as recited in claim 4, wherein the electrically transparent material comprises a polyvinyl material.

6. The device as recited in claim 5, wherein the electrically transparent material comprises polyethylene.

7. The device as recited in claim 1, wherein a point on the oscillation path of the probe is the closest approach of the probe to the epithelium.

8. The device as recited in claim 1, wherein the substantially constant distance is less than or equal to 500 μm.

9. The device as recited in claim 1, wherein the substantially constant distance is 20-500 μm.

10. The device as recited in claim 1, wherein the substantially constant distance is maintained to within a tolerance of about 6 μm.

11. The device as recited in claim 1, further comprising a microcontroller connected to said positioning device and a meter.

12. The device as recited in claim 1, wherein said bottom surface comprises a lens through which the epithelium is visible.

13. The device as recited in claim 12, further comprising a camera that provides a video image of the epithelium through the lens.

14. The device as recited in claim 1, wherein said vibration unit vibrates said probe at a frequency of 800 Hz to 1200 Hz.

15. The device as recited in claim 1, wherein said outer housing comprises a plastic material.

16. The device as recited in claim 1, wherein the first motor configured to move the probe in the x direction is configured to move the vibration unit in the x direction.

17. The device as recited in claim 1, wherein the first motor configured to move the probe in the x direction is configured to move the probe along a length of the aperture.

18. The device as recited in claim 17, wherein the first motor configured to move the probe in the x direction is configured to move the probe from one end of the aperture to another end of the aperture.

19. The device as recited in claim 1, wherein the first motor configured to move the probe in the x direction is disposed within the hand-held outer housing.

20. The device as recited in claim 1, wherein the first motor configured to move the probe in the x direction is a stepper motor.

* * * * *